United States Patent [19]

Yves et al.

[11] Patent Number: 4,978,776

[45] Date of Patent: Dec. 18, 1990

[54] PROCESS FOR THE MANUFACTURE OF METHYL METHACRYLATE FROM ISOBUTYRIC ACID

[75] Inventors: Samuel Yves, Saint Avold; Daniel Cauvy, Boulay, both of France

[73] Assignee: Norsolor, Cedex, France

[21] Appl. No.: 524,669

[22] Filed: May 15, 1990

Related U.S. Application Data

[63] Continuation of Ser. No. 394,084, Aug. 15, 1989, abandoned.

[30] Foreign Application Priority Data

Aug. 16, 1988 [FR] France .................................. 88 10911

[51] Int. Cl.$^5$ ........................ C07C 67/30; C07C 67/48
[52] U.S. Cl. ..................................... 560/214; 568/218
[58] Field of Search ................................. 560/214, 218

[56] References Cited

U.S. PATENT DOCUMENTS

| 2,541,486 | 2/1951 | Teeter et al. | 560/214 |
| 3,809,645 | 5/1974 | Matsuzawa et al. | 560/214 |
| 3,879,446 | 4/1975 | Blood et al. | 560/214 |
| 4,298,755 | 11/1981 | Daniel et al. | 560/214 |

FOREIGN PATENT DOCUMENTS

| 194541 | 9/1986 | European Pat. Off. |
| 995471 | 5/1963 | United Kingdom |

*Primary Examiner*—Paul J. Killos
*Attorney, Agent, or Firm*—Finnegan, Henderson Farabow, Garrett & Dunner

[57] ABSTRACT

A process for the manufacture of methyl methacrylate from isobutyric acid employing a catalytic oxidative dehydrogenation reaction in the vapor phase followed by condensation, liquid-liquid extraction, esterification, separation and purification steps.

13 Claims, 1 Drawing Sheet

PROCESS FOR THE MANUFACTURE OF METHYL METHACRYLATE FROM ISOBUTYRIC ACID

This application is a continuation of application Ser. No. 394,084 filed Aug. 15, 1989, abandoned.

FIELD OF THE INVENTION

The present invention relates to an improved process for the manufacture of methyl methacrylate from isobutyric acid.

BACKGROUND OF THE INVENTION

It is currently known to prepare methyl methacrylate from isobutyric acid by a two-stage process.

In the first stage, the oxidative dehydrogenation of isobutyric acid is carried out in the vapor phase at a temperature between 300° C. and 450° C. over a catalyst which may be either derived from iron phosphates as described, for example, in U.S. Pat. No. 4,298,755, or may be derived from phosphomolybdic acid as described for example in European Pat. No. 0,194,541.

The conversion of isobutyric acid is generally from 85% to 98%. Diluting water is generally necessary to keep the catalyst active, and water is formed during the reaction. The product leaving the oxidative dehydrogenation reactor, after condensation, consists chiefly of methacrylic acid, of unconverted isobutyric acid, of a greater or lesser proportion of water (25% to 85%), together with acetone and acetic acid in smaller proportions. A known manner of separating water from the organic acids consists in performing a liquid-liquid extraction. Many extraction solvents are described in the literature for this purpose: esters, ketones, aromatic solvents and mixtures thereof may be mentioned in particular.

However, a certain number of separations must still be carried out to obtain a methacrylic acid intended to be subjected to the second stage; thus, acetone must be removed and it is desirable to remove acetic acid and isobutyric acid as well.

In the second stage, the esterification of methacrylic acid with methanol to methyl methacrylate is carried out by an equilibrium reaction in liquid phase at a temperature from 70° C. to 130° C. in the presence of an acidic catalyst which may consist, for example, of sulfuric acid, of paratoluenesulfonic acid, of methanesulfonic acid or, preferably, of strong cationic resins. At the reactor outlet, methyl methacrylate, methacrylic acid, water and methanol are recovered possibly together with acetic and isobutyric acids and esters, depending on the degree of purification of the methacrylic acid introduced. A column is generally placed at the reactor outlet, enabling the unconverted acid or acids to be taken off so that they can be recycled to the esterification reactor.

Purification of methyl methacrylate is then performed according to known processes such as distillations, possibly a liquid-liquid extraction, and the like.

The process for the manufacture of methyl methacrylate in the form just described has the major disadvantage that isobutyric acid is incompletely converted into methacrylic acid in the first stage, with the result that the final methyl methacrylate contains methyl isobutyrate as an impurity in a quantity which is higher than the permitted limit for a methyl methacrylate to be considered as a high-purity commercial product. Such a product must, in fact, contain fewer than 100 parts per million of nonpolymerizable substances; it must, in other words, have a methyl isobutyrate content lower than this threshold of 100 parts per million.

Two possibilities offer themselves in order to obtain this very low content of methyl isobutyrate.

It is possible to consider separating methacrylic acid from isobutyric acid at the end of the first stage until a methacrylic acid of sufficient purity, that is to say containing fewer than 100 parts per million of isobutyric acid, is obtained. It is also possible for the isobutyric acid obtained at the head of the column to be then recycled to the oxidative dehydrogenation reactor to be combined with the initial isobutyric acid.

However, the technology of this distillation is difficult to implement. Measurements of liquid-vapor equilibrium show that, as a result of a nonideal thermodynamic behavior, the separation requires a very large number of theoretical plates. At the same time, because of the sensitivity of methacrylic acid to polymerization and of its high boiling point, this distillation must be conducted under high vacuum and using equipment which performs the separation with a very low pressure drop.

It is also possible to consider not modifying the first stage, in which case a mixture of methacrylic acid and unconverted isobutyric acid are introduced to carry out the esterification in the second stage. These acids are converted into esters in an equivalent proportion and methyl isobutyrate must then be separated form methyl methacrylate until the desired purity is obtained.

This separation offers a lesser technological difficulty than the separation of isobutyric acid, referred to above. On the other hand, on an industrial scale it is of no advantage to dispose of the methyl isobutyrate which would be recovered at the head of the column. Burning it leads to an unacceptable economic waste and, if it is recycled to the oxidative dehydrogenation reactor, the unconverted isobutyrate and the methyl methacrylate obtained will create a major disturbance in the first stage.

Therefore, neither of the above two possibilities in order to improve the known process with a view of obtaining methyl methacrylate of high purity appears to be satisfactory. Research has therefore been conducted for an acceptable solution to the problem which was presented and this has led to the present invention.

SUMMARY OF THE INVENTION

The subject of the invention is a process for the manufacture of methyl methacrylate from isobutyric acid, which process comprises:

subjecting isobutyric acid to a catalytic oxidative dehydrogenation in the vapor phase in an oxidative dehydrogenation stage to form a mixture of water, methacrylic acid and impurities including unconverted isobutyric acid;

condensing said mixture and carrying out a liquid-liquid extraction in an extraction stage to separate an aqueous phase containing the water, from an organic phase containing the acids obtained and impurities including acetone and methyl acetate;

esterifying said acids with methanol in an esterification stage to form a crude methyl methacrylate containing unesterified acids and containing methyl isobutyrate as an impurity, and using a fraction of the crude methyl methacrylate obtained as an extraction solvent in the extraction stage;

conveying the organic phase resulting from the extraction to a first separation stage which is located downstream of the esterification stage, and separating the organic phase to provide:

(1) crude methyl methacrylate consisting of the fraction of methyl methacrylate produced by esterification including the fraction thereof employed as an extraction solvent; and (2) the organic acids consisting of the acids obtained at the end of oxidative dehydrogenation and the unesterified acids;

recycling said organic acids to the esterification stage; and purifying the fraction of crude methyl methacrylate which was not employed as extraction solvent by separating pure methyl methacrylate and methyl isobutyrate in a second separation stage and recycling the methyl isobutyrate to the oxidative dehydrogenation stage.

As seen from the foregoing, the starting isobutyric acid is subjected to a catalytic oxidative dehydrogenation in the vapor phase, leading to a mixture of water, methacrylic acid and impurities, including unconverted isobutyric acid. The mixture is condensed and a liquid-liquid extraction is carried out in order to separate an aqueous phase containing the water from the organic acids obtained.

An esterification of the acids with methanol is carried out, leading to a crude methyl methacrylate, one of the impurities in which is methyl isobutyrate.

The process is characterized in that the liquid-liquid extraction is carried out using a fraction of the crude methyl methacrylate obtained in the esterification reaction; the organic phase resulting from this extraction is conveyed to a separation stage situated immediately downstream of the esterification stage, making it possible to separate, on the one hand, the crude methyl methacrylate consisting of the fraction of methyl methacrylate produced by esterification and that employed as the extraction solvent and, on the other hand, the organic acids consisting of the fraction of the organic acids obtained at the end of oxidative dehydrogenation and that of the unesterified acids which are thus recycled, and purification of the fraction of crude methyl methacrylate which has not been employed as the extraction solvent is carried out in order to separate, on the one hand, pure methyl methacrylate and, on the other hand, methyl isobutyrate, which is recycled to the oxidative dehydrogenation stage.

In accordance with specific embodiments of this process:

the organic phase originating from the liquid-liquid extraction stage is separated from the impurities consisting of acetone and methyl acetate before the phase is sent to a crude methyl methacrylate/organic acids (first) separation stage;

a crude methyl methacrylate effluent is separated from its residual water before the effluent is sent back to the extraction stage and to a crude methyl methacrylate/methyl isobutyrate (second) separation stage;

furthermore, provision may be made for recycling a fraction of the crude methyl methacrylate effluent, separated from residual water, as a reflux to the crude methyl methacrylate/organic acids (first) separation stage;

an additional purification of the methyl methacrylate obtained from the crude methyl methacrylate/methyl isobutyrate (second) separation stage, the heavy products separated being, if appropriate, recycled to the crude methyl methacrylate/organic acids (first) separation stage;

the aqueous phase taken from the extraction stage is recycled to the oxidative dehydrogenation stage after the aqueous phase has been subjected to a stripping operation making it possible to separate off any remaining organic phase therein which is recycled to the esterification stage, and after having removed from the aqueous phase purified by the stripping operation a purge which is substantially equal to the water formed by the oxidative dehydrogenation and esterification reactions; and furthermore, the residual water which it has been possible to extract from the crude methyl methacrylate effluent can be recycled to the stripping stage.

BRIEF DESCRIPTION OF THE DRAWING

The accompanying drawing is a schematic general arrangement and process flow sheet in which the process of present invention was conducted.

DETAILED DESCRIPTION OF THE INVENTION

Figure 1:
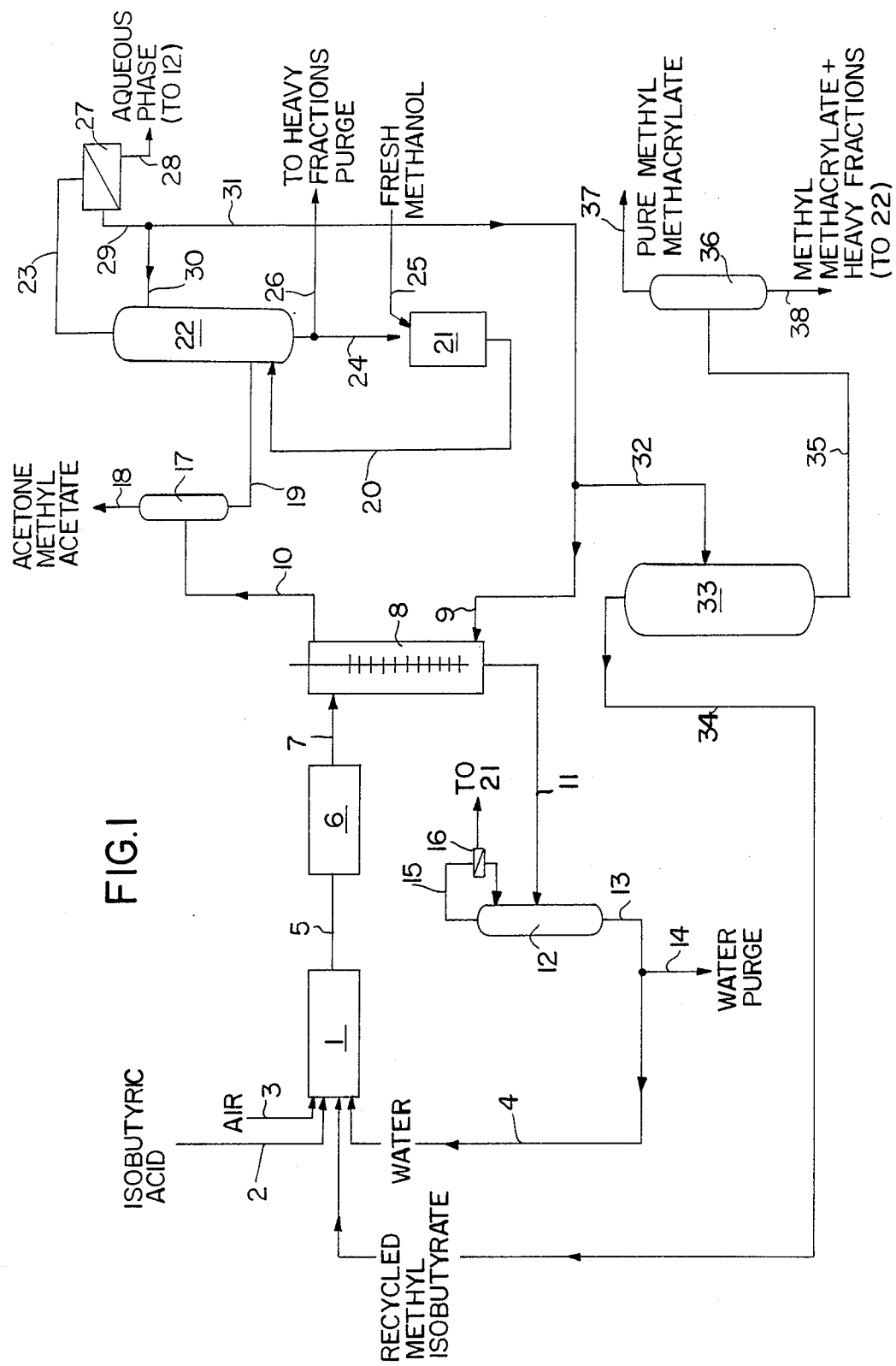

The invention will also be illustrated by the description which follows, a preferred embodiment, given with reference to the attached drawing which shows the operating diagram of the process in accordance with this preferred embodiment.

In reactor 1, the catalytic oxidative dehydrogenation of isobutyric acid in the vapor phase is carried out in a conventional manner; reactor 1 is fed with isobutyric acid via line 2, with air via line 3, and with water via line 4 which forms a recycle line as will be described later. Dilution water is necessary, in fact, to keep the catalyst active, the catalyst being chosen especially from the substances referred to above.

The effluent leaving reactor 1 through line 5 is a gaseous effluent consisting of a mixture of dilution water to which is added the water formed during the reaction, and of organic substances consisting chiefly of methacrylic acid, which is the required product, and, in lesser proportions, unconverted isobutyric acid and, as by-products, acetone, methyl acetate and acetic acid.

This gaseous effluent 5 is condensed in condenser 6 and the condensate 7 is then sent to a liquid-liquid extraction column 8. The solvent entering the lower part of the extraction column 8 via extraction line 9 consists of a recycled fraction of crude methyl methacrylate, as will be described later. An organic phase is obtained and conveyed through line 10 at the head of the extraction column 8 and an aqueous phase is taken off through line 11 at the lower part of column 8.

This aqueous phase is sent and introduced halfway up a stripping column 12, from the lower part of which is taken off an aqueous phase circulating in the line 13. A water purge in particular of water from the oxidative dehydrogenation reactor 1 and esterification reactor 21, is arranged in line 13; this water, which may undergo a pretreatment, can be disposed of via line 14 to the natural environment. There is obtained an aqueous effluent which is recycled via line 4 to the oxidative dehydrogenation reactor 1. An organic phase leaves via line 15 at the head of the stripping column 12 and this, after condensation in condenser 16 is recycled to the esterification reactor 21, which will be described later.

As for the organic phase leaving via line 10 at the head of the liquid-liquid extraction column 8, this is sent and introduced half way up a distillation column 17, at the head of which the impurities consisting of acetone and methyl acetate are removed, as shown diagrammatically via line 18. The acetic acid present in the system is either oxidized in the oxidative dehydrogenation reactor 1 or is subsequently converted into methyl acetate in the esterification reactor 21 described later, and is finally removed via line 18.

The effluent leaving the lower part of column 17 via line 19 is sent to a distillation column 22 which also receives via line 20, at a lower point, a stream leaving the esterification reactor 21, said stream consisting chiefly of methyl methacrylate, and to a lesser extent unconverted methacrylic acid, unconverted isobutyric acid, water and impurities. In an alternative form, the effluent in line 19 is combined with the stream in line 20, the resulting combined stream being sent to the column 22. Crude methyl methacrylate is separated off in the upper part of the column 22, through the line 23, and the organic acids (methacrylic acid and, to a lesser extent, isobutyric acid) are taken off through the line 24 in the lower part of the column 22 and are sent to the esterification reactor 21. The fresh methanol feed is shown diagrammatically as being introduced by line 25. However, the organic acids in line 24 sent to the esterification reactor 21 are subjected, before entering the reactor 21, to a purge intended to remove heavy substances, as shown diagrammatically at line 26.

The effluent in the line 23 is condensed in condenser 27 from which there is separated, on the one hand, via line 28, an aqueous phase which is advantageously recycled to the stripping column 12, via a line which is not shown in order to simplify the drawing, and, on the other hand, via line 29, crude methyl methacrylate. The crude methyl methacrylate is partly recycled as a reflux, through line 30, to the head of column 22, and partly sent, via line 31, on the one hand, through line 9, to the liquid-liquid extraction column 8 and, on the other hand, through line 32, to a methyl methacrylate/methyl isobutyrate separation stage in column 33. Thus, methyl isobutyrate is taken from the upper part of the distillation column 33 to be recycled to the oxidative dehydrogenation reactor 1 through line 34, and purified methyl methacrylate is taken from the lower part of column 33, through line 35, to be sent and introduced halfway up a second column 36, with a view to an additional purification which makes it possible to obtain very pure methyl methacrylate at the head, though line 37, and, at the foot of the column, through line 38, methyl methacrylate in combination with heavy fractions, which is advantageously recycled towards the distillation column 22, through a line which is not shown, in order to simplify the drawing.

It is readily apparent that the embodiment described above has been given by way of guidance and that modifications can be introduced without departing thereby from the scope of the invention.

What is claimed is:

1. A process for the manufacture of methyl methacrylate from isobutyric acid, which process comprises:
   subjecting isobutyric acid to a catalytic oxidative dehydrogenation in the vapor phase in an oxidative dehydrogenation stage to form a mixture of water, methacrylic acid and impurities including unconverted isobutyric acid;
   condensing said mixture and carrying out a liquid-liquid extraction in an extraction stage to separate an aqueous phase containing the water, from an organic phase containing the acids obtained and impurities including acetone and methyl acetate;
   esterifying said acids with methanol in an esterification stage to form a crude methyl methacrylate containing unesterified acids and containing methyl isobutyrate as an impurity, and using a fraction of the crude methyl methacrylate obtained as an extraction solvent in the extraction stage;
   conveying the organic phase resulting from the extraction to a first separation stage which is located downstream of the esterification stage, and separating the organic phase to provide:
   (1) crude methyl methacrylate consisting of the fraction of methyl methacrylate produced by esterification including the fraction thereof employed as an extraction solvent; and
   (2) the organic acids consisting of the acids obtained at the end of oxidative dehydrogenation and the unesterified acids;
   recycling said organic acids to the esterification stage; and
   purifying the fraction of crude methyl methacrylate which was not employed as extraction solvent by separating pure methyl methacrylate and methyl isobutyrate in a second separation stage and recycling the methyl isobutyrate to the oxidative dehydrogenation stage.

2. The process according to claim 1, further comprising separating the organic phase obtained from the liquid-liquid extraction stage from the acetone and methyl acetate impurities before said organic phase is conveyed to the first separation stage.

3. The process according claim 1, further comprising separating the crude methyl methacrylate obtained from the first separation stage from any residual water before said crude methyl methacrylate is used in the extraction stage and purified in the second separation stage.

4. The process according to claim 3, further comprising recycling a fraction of the crude methyl methacrylate as a reflux to the first separation stage.

5. The process according to claim 4, comprising further purifying the methyl methacrylate obtained at the second separation stage and recycling any heavy products separated to the first separation stage.

6. The process according to claim 3, comprising further purifying the methyl methacrylate obtained at the second separation stage and recycling any heavy products separated to the first separation stage.

7. The process according to claim 2, comprising further purifying the methyl methacrylate obtained at the second separation stage and recycling any heavy products separated to the first separation stage.

8. The process according to claim 1, comprising further purifying the methyl methacrylate obtained at the second separation stage and recycling any heavy products separated to the first separation stage.

9. The process according to claim 1, further comprising stripping the aqueous phase from the extraction stage in a stripping stage to separate any remaining organic phase therein and recycling said organic phase to the extraction stage; and
   purging from the remaining aqueous phase of an amount thereof substantially equal to the water formed in the oxidative dehydrogenation and esterification stages.

10. The process according to claim 3, further comprising stripping the aqueous phase from the extraction stage in a stripping stage to separate any remaining organic phase therein and recycling said organic phase to the extraction stage; and purging from the remaining aqueous phase of an amount thereof substantially equal to the water formed in the oxidative dehydrogenation and esterification stages.

11. The process according to claim 10, further comprising recycling the residual water extracted from the crude methyl methacrylate to the stripping stage.

12. The process according to claim 2, further comprising conveying the crude methyl methacrylate leaving the esterification stage to the first separation stage at a point lower than that to which is conveyed the said organic phase.

13. The process according to claim 2, further comprising combining the crude methyl methacrylate leaving the esterification stage with the said organic phase and conveying the combined methyl methacrylate and organic phase to the first separation stage.

* * * * *